US012564715B2

(12) United States Patent
Gurfein et al.

(10) Patent No.: US 12,564,715 B2
(45) Date of Patent: Mar. 3, 2026

(54) TMJ TREATMENT DEVICE WITH ADAPTIVE CIRCUIT

(71) Applicant: TIVIC HEALTH SYSTEMS INC., Menlo Park, CA (US)

(72) Inventors: Blake Taylor Gurfein, San Rafael, CA (US); John Claude, Redwood City, CA (US); Christopher A. Wiklof, Everett, WA (US)

(73) Assignee: Tivic Health Systems Inc., Menlo Park, CA (US)

( * ) Notice: Subject to any disclaimer, the term of this patent is extended or adjusted under 35 U.S.C. 154(b) by 305 days.

(21) Appl. No.: 18/343,848

(22) Filed: Jun. 29, 2023

(65) Prior Publication Data

US 2024/0017062 A1 Jan. 18, 2024

Related U.S. Application Data

(63) Continuation of application No. PCT/US2022/029481, filed on May 16, 2022.

(60) Provisional application No. 63/189,004, filed on May 14, 2021.

(51) Int. Cl.
*A61N 1/36* (2006.01)
*A61N 1/04* (2006.01)

(52) U.S. Cl.
CPC ....... *A61N 1/36021* (2013.01); *A61N 1/0456* (2013.01); *A61N 1/36031* (2017.08); *A61N 1/36034* (2017.08)

(58) Field of Classification Search
None
See application file for complete search history.

(56) References Cited

U.S. PATENT DOCUMENTS

| | | | | |
|---|---|---|---|---|
| 4,586,509 A | * | 5/1986 | Liss | A61N 1/36021 607/46 |
| 2019/0217088 A1 | * | 7/2019 | Claude | A61N 1/0456 |

FOREIGN PATENT DOCUMENTS

| | | |
|---|---|---|
| JP | 2015-47365 A | 3/2015 |
| KR | 10-1280438 B1 | 6/2013 |
| WO | 2009155516 A2 | 12/2009 |
| WO | 2018200443 A1 | 11/2018 |

OTHER PUBLICATIONS

Kato, Melissa Thiemi et al., Tens and Low-Level Laser Therapy in the Management of Temporomandibuar Disorders; J. Appl. Oral Sci. 2006; 14(20: 130-5.

* cited by examiner

*Primary Examiner* — George R Evanisko

(74) *Attorney, Agent, or Firm* — Launchpad IP, Inc.; Christopher A. Wiklof; James C. Larsen

(57) ABSTRACT

A temporomandibular joint (TMJ) disorder microcurrent treatment device and methods of operating the microcurrent device that includes a treatment electrode and at least one return electrode. The TMJ microcurrent treatment device may output and maintain a constant current treatment waveform.

20 Claims, 9 Drawing Sheets

Mandibular zone

Maxillary zone

Ophthalmic zone

Trigeminal nerve

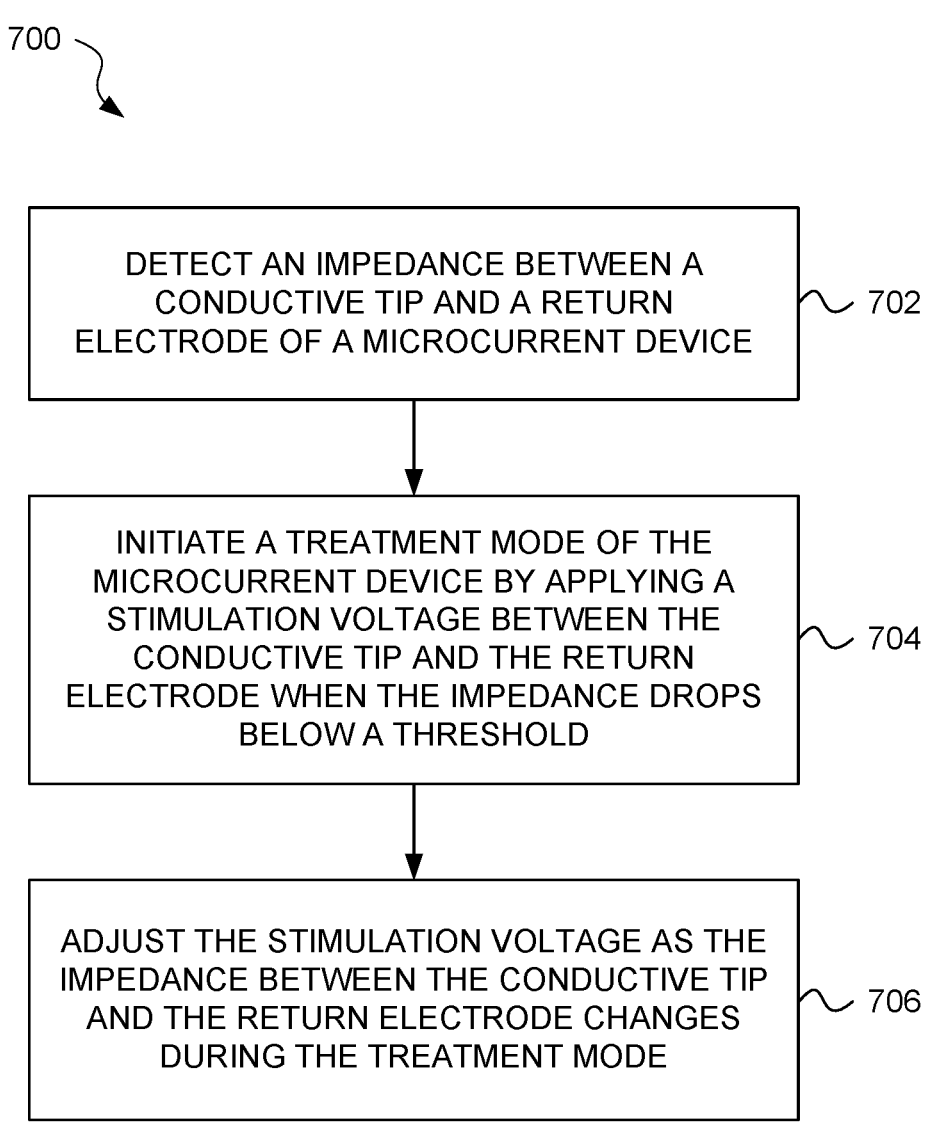

700

DETECT AN IMPEDANCE BETWEEN A CONDUCTIVE TIP AND A RETURN ELECTRODE OF A MICROCURRENT DEVICE ⟿ 702

INITIATE A TREATMENT MODE OF THE MICROCURRENT DEVICE BY APPLYING A STIMULATION VOLTAGE BETWEEN THE CONDUCTIVE TIP AND THE RETURN ELECTRODE WHEN THE IMPEDANCE DROPS BELOW A THRESHOLD ⟿ 704

ADJUST THE STIMULATION VOLTAGE AS THE IMPEDANCE BETWEEN THE CONDUCTIVE TIP AND THE RETURN ELECTRODE CHANGES DURING THE TREATMENT MODE ⟿ 706

TMJ TREATMENT DEVICE WITH ADAPTIVE CIRCUIT

CROSS REFERENCE TO RELATED APPLICATIONS

The present application is a Continuation application which claims priority benefit under 35 U.S.C. § 120 of co-pending International PCT Patent Application No. PCT/US2022/029481, entitled "TMJ TREATMENT DEVICE WITH ADAPTIVE CIRCUIT, filed May 16, 2022; which claims priority benefit from U.S. Provisional Patent Application No. 63/189,004, entitled "TMJ TREATMENT DEVICE WITH ADAPTIVE CIRCUIT," filed May 14, 2021, each of which, to the extent not inconsistent with the disclosure herein, is incorporated by reference.

BACKGROUND

Every year, millions of people suffer from temporomandibular joint (TMJ) pain. TMJ pain may cause symptoms expressed as pain associated with the jaw, and/or as reduced movement range of the jaw, as musculature becomes swollen and/or inflamed. Typical TMJ therapy includes systemic medications such as muscle relaxants that may be taken orally but which may also have significant side effects including drowsiness.

What is needed is an approach that may alleviate TMJ disorders without the negative effects of conventional TMJ medications.

SUMMARY

According to an embodiment, a method of operating a temporomandibular joint (TMJ) disorder treatment device includes applying a treatment electrode of a microcurrent device to a user's skin superjacent to the user's maxillary and/or mandibular nerve, applying a stimulation voltage between the treatment electrode and a return electrode, detecting an impedance between the treatment electrode and the return electrode of the microcurrent device, and initiating a treatment mode of the microcurrent device by initiating a user interface notification that the treatment electrode is at a treatment location when the impedance drops below a threshold. The method of operating the microcurrent device may also include adjusting the stimulation voltage as the impedance between the treatment electrode and the return electrode changes during the treatment mode. The application of the microcurrent waveform at least partially through the maxillary and/or mandibular nerve as a recurring therapy is understood to provide relief from TMJ disorders.

According to an embodiment, a method of operating a microcurrent device includes measuring a stimulation signal from a treatment electrode of the microcurrent device. The stimulation signal is representative of a stimulation current between the treatment electrode and a return electrode attached with a device body or housing of the microcurrent device. The method of operating the microcurrent device also includes adjusting a stimulation voltage across the treatment electrode and the return electrode to keep the stimulation current at a constant value. Optionally, maintaining constant current may include measuring the stimulation signal.

According to an embodiment, a microcurrent device includes a device body or housing, a treatment electrode, a return electrode operatively coupled to the device body of the microcurrent device, and a stimulation driver stage coupled to apply a stimulation voltage between the treatment electrode and the return electrode. The operatively coupled return electrode may include a metal adhered or plated onto a dielectric device body, conductive particles embedded in the device body, an inherently conductive device body, and/or an aperture in the device body. The device body may be configured to physically support the return electrode. A signal from the driver stage may be transmitted through the device body to the return electrode.

According to an embodiment, the microcurrent device includes a peak detector coupled to generate a peak stimulation current signal in response to receiving a feedback stimulation signal from the treatment electrodes, and a microcontroller coupled to receive the peak stimulation current signal from the peak detector. The microcontroller may be coupled to the stimulation driver stage for adjusting the stimulation voltage in response to the peak stimulation current signal. The microcontroller may dynamically adjust the stimulation voltage to keep the peak stimulation current signal at a constant or substantially constant value.

BRIEF DESCRIPTION OF THE DRAWINGS

FIG. 5 illustrates an example adaptive output circuit for use with a microcurrent device, according to an embodiment of the disclosure.

FIG. 7 is a flow chart illustrating an example process of operating a handheld microcurrent device, according to an embodiment of the disclosure.

DETAILED DESCRIPTION

Figure 1A:
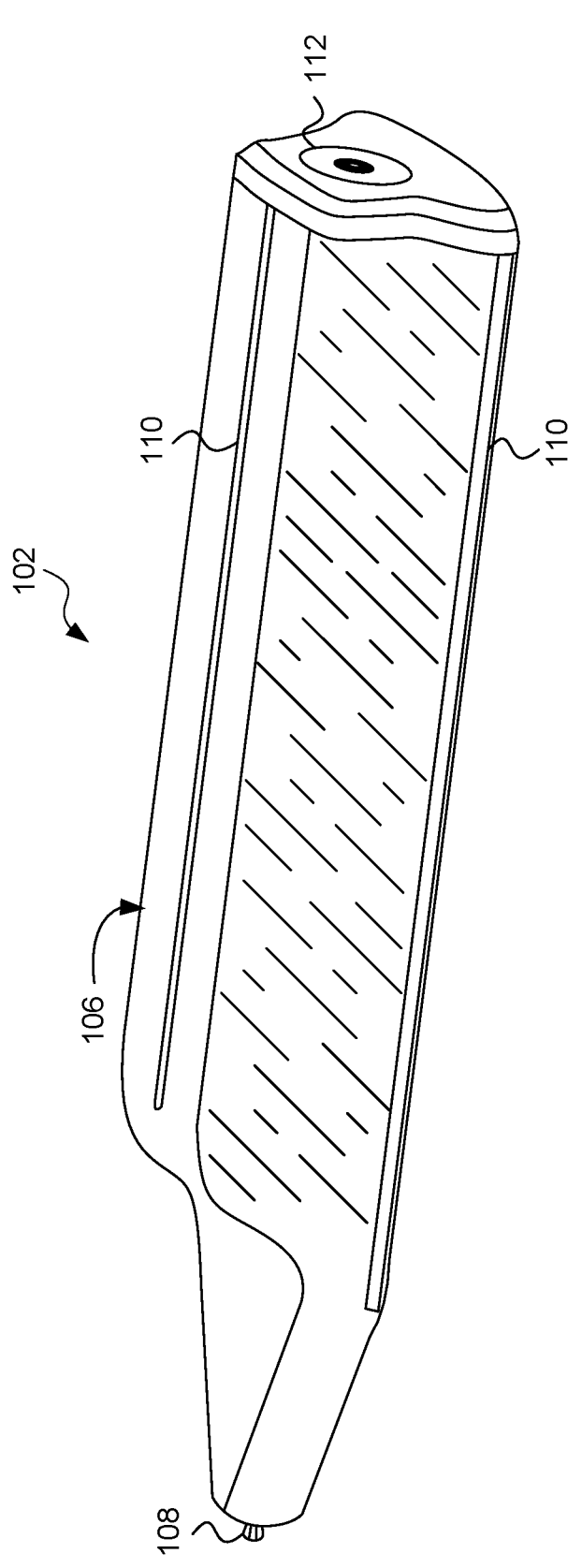
FIG. 1A is a perspective view of a handheld temporomandibular joint (TMJ) treatment microcurrent device, according to an embodiment of the disclosure.

In the following detailed description, reference is made to the accompanying drawings, which form a part hereof. In the drawings, similar symbols typically identify similar components, unless context dictates otherwise. Other embodiments may be used and/or other changes may be made without departing from the spirit or scope of the disclosure.

FIG. 1A is a perspective view of a handheld temporomandibular joint (TMJ) treatment microcurrent device 102, according to an embodiment. The handheld microcurrent device 102 includes a device body 106, a treatment electrode 108, a return electrode 110, and a charging port 112, according to an embodiment.

According to an embodiment, the handheld microcurrent device 102 is configured to provide TMJ disorder treatment to a user. The user holds the microcurrent device 102 in one hand, with the hand contacting the return electrode 110, places the treatment electrode 108 against the skin in a treatment region (see FIG. 3) and, in a detection mode, glides the treatment electrode 108 across the skin until the handheld microcurrent device 102 detects a treatment location. When the handheld microcurrent device 102 detects a treatment location, the handheld microcurrent device 102 enters a treatment mode, directs the user to hold the handheld microcurrent device 102 still while a stimulation current flows (e.g., continues to flow) between the treatment electrode 108 and the return electrode 110. The stimulation current passes through a nerve at the treatment location, thereby providing relief to the user. It is also believed that additional relief is caused by passing the stimulation current through muscles, tendons, ligaments, insertions, and/or other connective tissue in and around the TMJ. According to one embodiment, the handheld microcurrent device 102 commences outputting a therapeutic strength stimulation current when the device 102 enters the treatment mode. In another embodiment, the therapeutic current is constantly output during both the detection mode and the treatment mode, and entering the treatment mode consists of outputting a signal to the user, for example in the form of a flashing LED and/or vibrating, haptic indicator, indicating that the microcurrent device 102 has entered the treatment mode.

According to an embodiment, the device body 106 is a rigid casing or housing. The device body 106 has a shape that enables the user of the handheld microcurrent device 102 to securely grip and comfortably hold the handheld microcurrent device 102 during operation of the handheld microcurrent device 102.

In one embodiment, the device body 106 may be made from a material that is not electrically conductive. Alternatively, the device body 106 may be made from a material that is electrically conductive, or may include portions that are electrically conducive, according to an embodiment. The device body 106 may be made from a material that has low thermal conductivity. The device body 106 is configured to protect sensitive electronic circuitry positioned within the device body 106, as is described in more detail with relation to FIGS. 4-5.

According to an embodiment, the treatment electrode 108 is an electrical conductor placed at a tip of the device body 106. The treatment electrode 108 may include a rounded shape at a point of contact with the skin of the user such that the treatment electrode 108 can be placed against the skin of the user comfortably without piercing or scratching the skin. Furthermore, the shape and material of the treatment electrode 108 may be selected to enable the user to comfortably glide the treatment electrode 108 along the skin of the user's face and jaw. The treatment electrode 108 may alternatively be referred to as a therapeutic electrode or conductive tip.

According to an embodiment, the return electrode 110 includes an electrically conductive material positioned at various locations on or in the device body 106. The return electrode 110 may be positioned in the device body 106 at positions selected so that when the user holds the handheld microcurrent device 102 in the user's hand, the user's hand is in contact with the return electrode 110 on one or more locations on the device body 106. According to an embodiment, the return electrode 110 may include a conductive polycarbonate.

According to an embodiment, the charging port 112 is positioned at the rear of the device body 106 of the handheld microcurrent device 102. The charging port 112 is configured to receive a charging cable. When the charging cable is connected to the charging port 112, the internal battery of the handheld microcurrent device 102 is recharged. Additionally, or alternatively, the charging port 112 may be a power supply port configured to connect to a power cable that provides power to the handheld microcurrent device 102 while the user is using the handheld microcurrent device 102. The charging port 112 may be a micro USB port, a USB 2.0 port, a USB 3.0 port, a USB C port, or any other kind of port that may be utilized to charge the battery of the handheld microcurrent device 102, or to otherwise provide power to the handheld microcurrent device 102. Additionally, or alternatively, the handheld microcurrent device 102 may include wireless charging capability. For example, the handheld microcurrent device 102 may include circuitry that enables inductive charging of the battery of the handheld microcurrent device 102 such that when the handheld microcurrent device 102 is positioned on a charging dock, the battery is recharged by inductive charging.

Figure 1B:
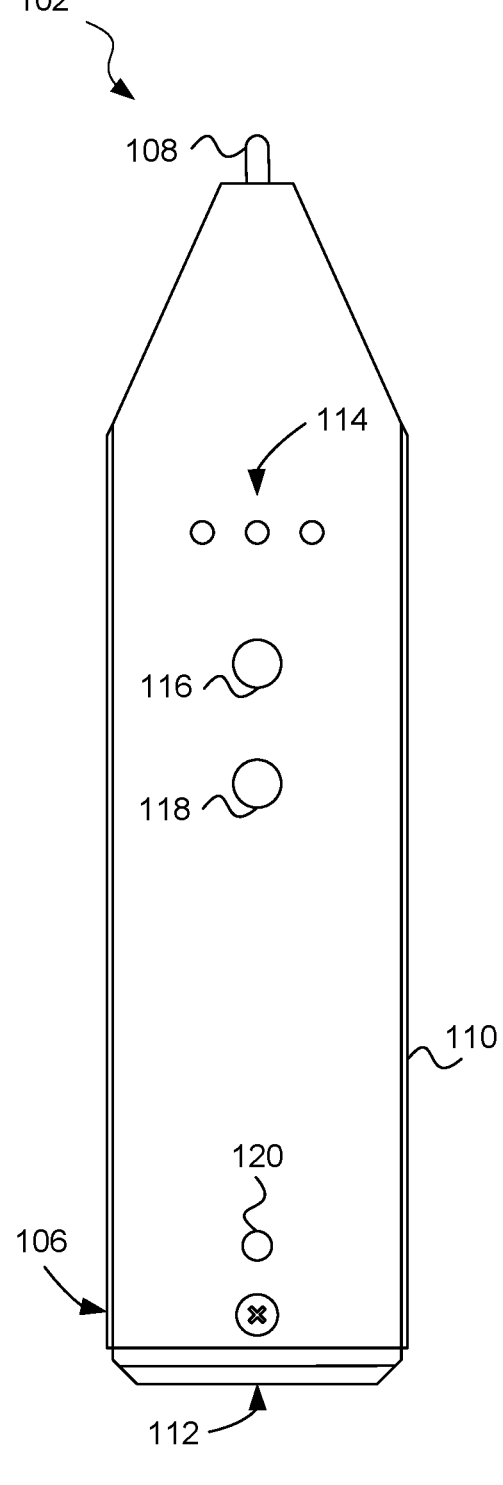
FIG. 1B is a top view of the handheld microcurrent device of FIG. 1A, according to an embodiment of the disclosure.

FIG. 1B is a top view of a handheld microcurrent device 102, according to an embodiment. The top view of the handheld microcurrent device 102 illustrates the device body 106, the treatment electrode 108, the return electrode 110, indicators 114, a sensitivity setting button 116, a power button 118, and a low battery indicator 120.

According to an embodiment, the indicators 114 may provide an indication of the sensitivity level of the handheld microcurrent device 102. The sensitivity level corresponds to a sensitivity setting for detecting treatment areas of the user. The indicators 114 may include multiple LED indicators. The handheld microcurrent device 102 may illuminate a number of the sensitivity level indicator LEDs 114 to indicate a sensitivity level of the handheld microcurrent device 102 during a detection mode. A greater number of illuminated indicator LEDs 114 may correspond to a higher sensitivity level. A lesser number of illuminated indicator LEDs 114 may correspond to a lower sensitivity level. Alternatively, other schemes for illuminating LEDs to indicate a sensitivity level of the detection mode of the handheld microcurrent device 102 may be utilized. Additionally, the indicators 114 may include indicators other than LEDs. For example, the indicators 114 may include various types of lights, a display panel, or other types of indicators capable of providing an indication of the sensitivity level of the handheld microcurrent device 102 during a detection mode of the handheld microcurrent device 102. According to an embodiment, the indicators 114 may also signal that a treatment location has been identified, that treatment stimulation is currently being provided, that another treatment location should be identified, or other parameters of operation of the handheld microcurrent device 102.

According to an embodiment, the sensitivity setting button 116 is configured to enable the user to adjust the sensitivity of the handheld microcurrent device 102 during a detection mode. The user may manipulate the sensitivity setting button 116 in order to increase or decrease the sensitivity of the handheld microcurrent device 102. For example, the user may press the sensitivity setting button 116 to adjust the sensitivity of the handheld microcurrent device 102. Additionally, or alternatively, the user may toggle or slide the sensitivity setting button 116 in order to adjust the sensitivity of the handheld microcurrent device 102. Additionally, or alternatively, the sensitivity setting button 116 may include multiple buttons for adjusting the sensitivity of the handheld microcurrent device 102. A first button may be used to decrease the sensitivity. A second button may be used to increase the sensitivity. Additionally, or alternatively, the handheld microcurrent device 102 may include a touchscreen that enables the user to adjust the sensitivity of the handheld microcurrent device 102.

According to an embodiment, the power button 118 is configured to enable the user to turn the handheld microcurrent device 102 on or off. For example, if the handheld microcurrent device 102 is currently off, then the user may turn the handheld microcurrent device 102 on by pressing, toggling, sliding, or otherwise manipulating, the power button 118. If the handheld microcurrent device 102 is currently on, then the user may turn the handheld microcurrent device 102 off by pressing, toggling, sliding, or otherwise manipulating the power button 118. Alternatively, the sensitivity setting button 116 and the power button 118 may be implemented in a single button or switch that may adjust the sensitivity or turn the handheld microcurrent device 102 on or off based on a length of a button press, a number of button presses, or other types of manipulations of the single button.

According to an embodiment, the low battery indicator 120 may provide an indication of a state of charge of the battery of the handheld microcurrent device 102. The low battery indicator 120 may include one or more LEDs. When the battery of the handheld microcurrent device 102 is low, one or more LEDs of the low battery indicator 120 may become illuminated. If the low battery indicator 120 includes a single LED, then the single LED may become illuminated when the battery is nearing depletion. Conversely, the single LED may not be illuminated when the battery is not nearing depletion. Alternatively, when the battery is nearing depletion, a first LED of a first color may be illuminated to indicate that the battery is nearing depletion. If the battery is not nearing depletion, then a second LED of a second color may be illuminated indicating that the battery is not nearing depletion.

According to an embodiment, portions of the return electrode 110 are positioned on the sides of the device body 106 of the handheld microcurrent device 102. When the user grips the handheld microcurrent device 102 such that a thumb of the user is in a position to manipulate the sensitivity setting button 116 and the power button 118, the palm and/or fingers of the hand of the user will be in contact with the portion of the return electrode 110 positioned on the sides of the device body 106 of the handheld microcurrent device 102.

Figure 1C:
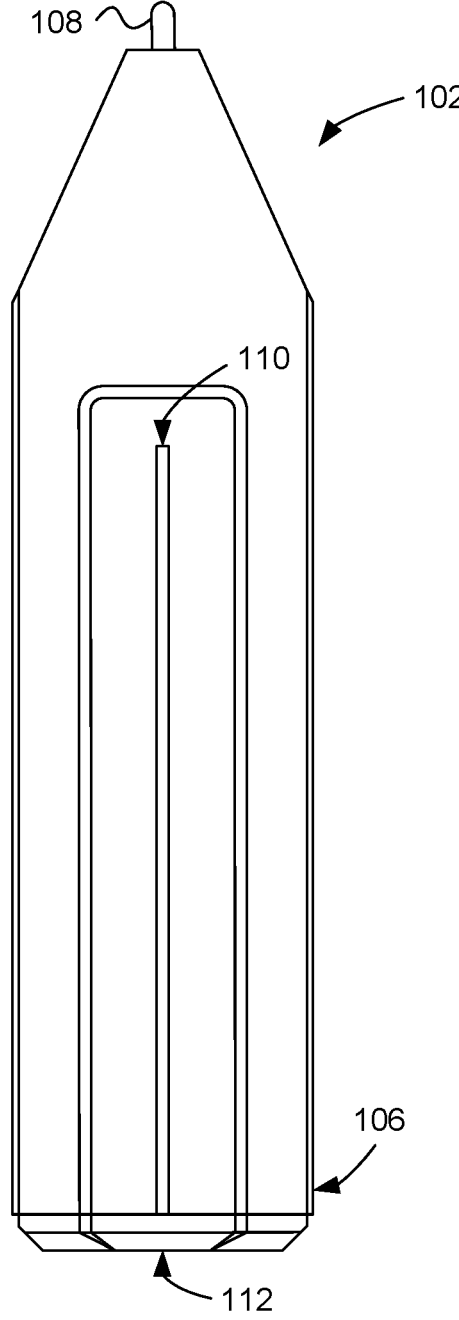
FIG. 1C is a bottom view of the handheld microcurrent device of FIG. 1A, according to an embodiment of the disclosure.

FIG. 1C is a bottom view of the handheld microcurrent device 102 of FIG. 1B, according to an embodiment. The bottom view of the handheld microcurrent device 102 illustrates a portion of the return electrode 110 positioned on the bottom portion of the device body 106 of the handheld microcurrent device 102. The positioning of a portion of the return electrode 110 on the bottom of the device body 106 of the handheld microcurrent device 102 further ensures that when the user holds the handheld microcurrent device 102 in the user's hand, the user's hand will be in contact with the return electrode 110.

Figure 2:
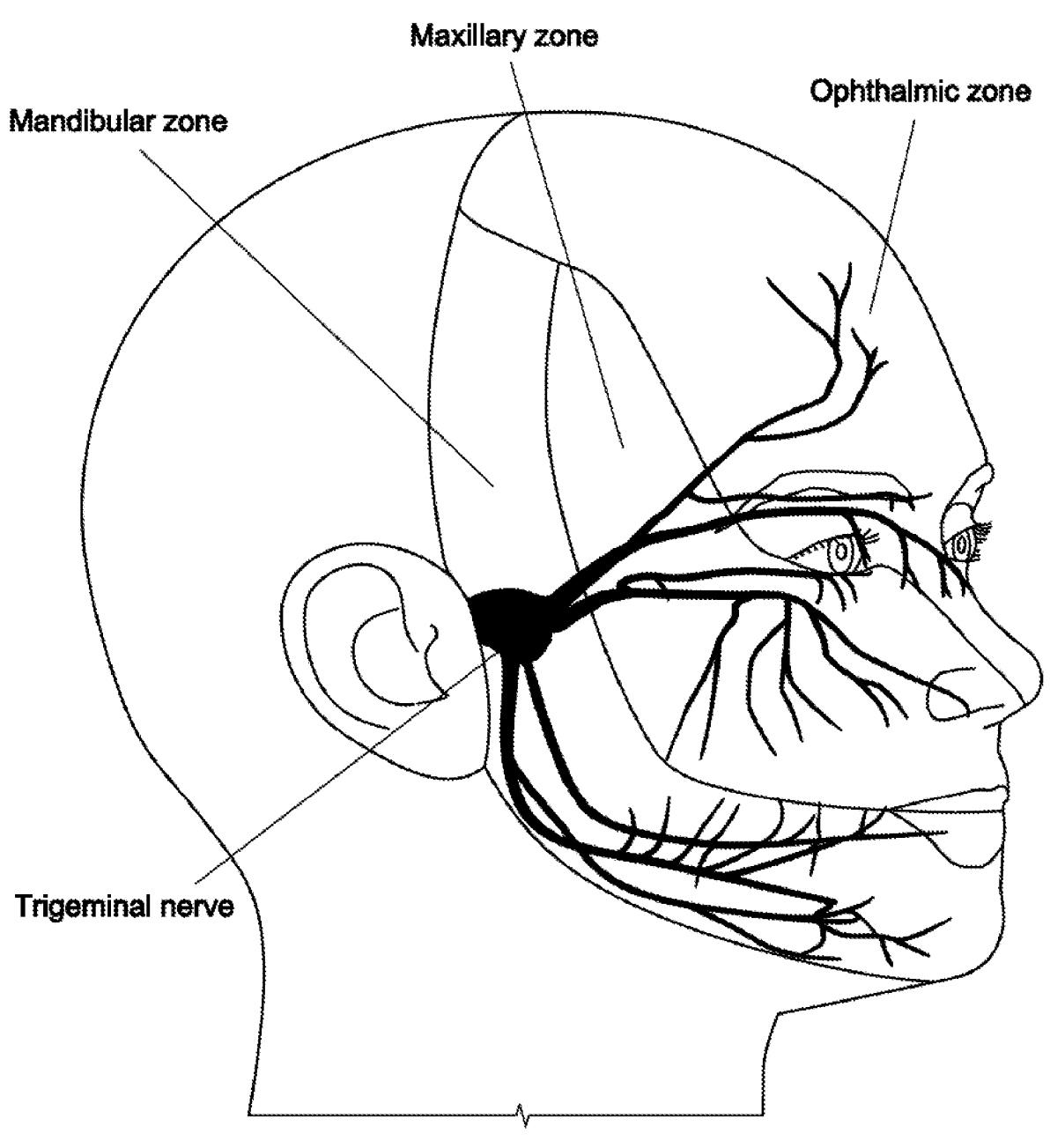
FIG. 2 is an illustration of an anatomy of nerves lying below the skin of the head and neck of a human.

FIG. 2 is an illustration of an anatomy of nerves lying below the skin of the head and neck of a human.

Figure 3:
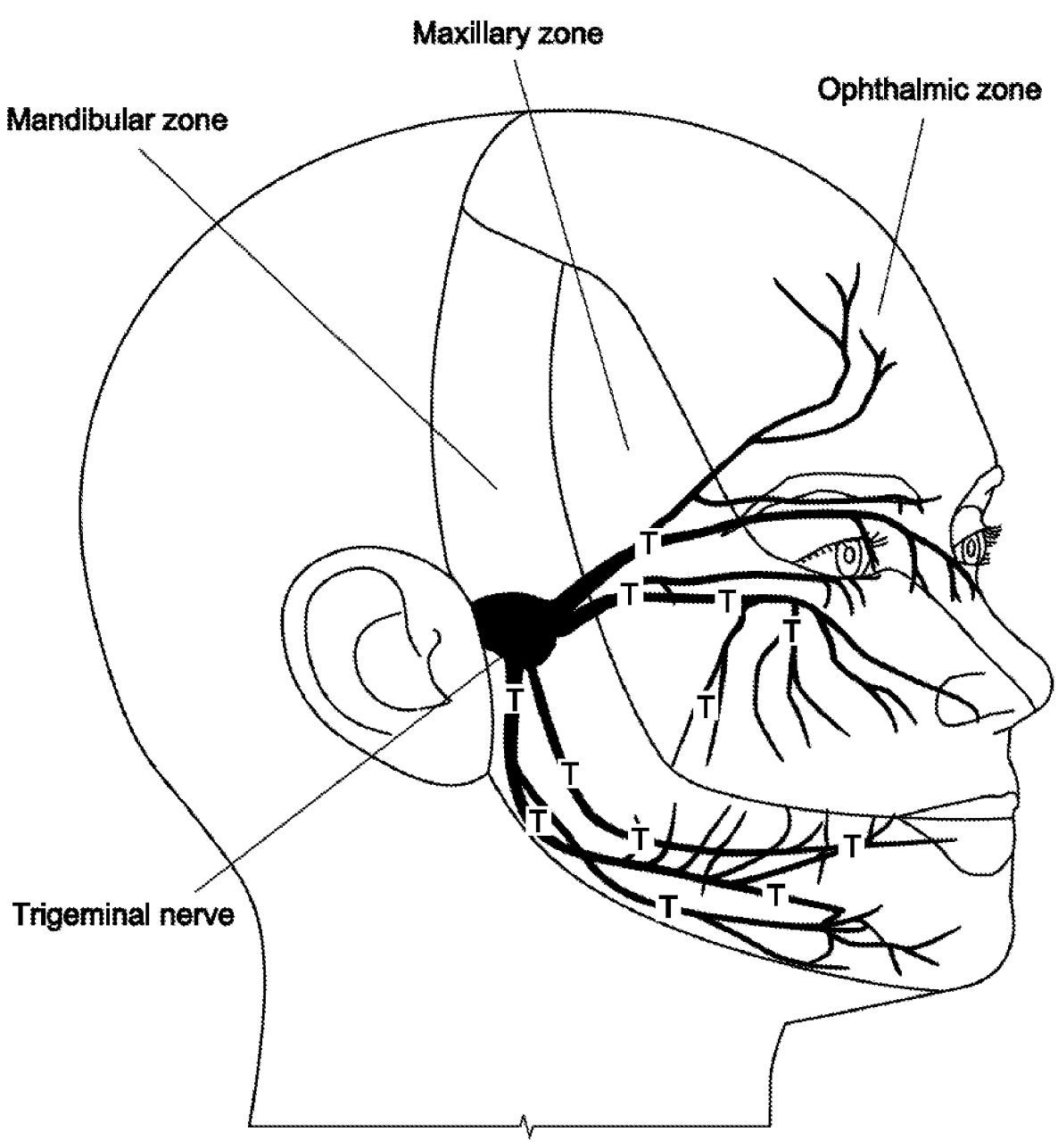
FIG. 3 illustrates nerves that a microcurrent device may be applied to, according to an embodiment of the disclosure.

FIG. 3 is an illustration of a profile of a user of the handheld microcurrent device 102 (e.g., see FIGS. 1A-1C) highlighting treatment areas T. According to an embodiment, the treatment areas T correspond to regions of the maxillary and/or mandibular nerve.

According to an embodiment, the user uses the handheld microcurrent device 102 by holding the device body 106 in one hand such that the user's hand is in contact with portions of the return electrode 110. The user then places the treatment electrode 108 on the skin and glides the treatment electrode 108 over the skin during a detection mode of the handheld microcurrent device 102. In the detection mode, the handheld microcurrent device 102 detects a treatment location T, corresponding to a location of a portion of the maxillary and/or mandibular nerve beneath the skin. When the handheld microcurrent device 102 detects the treatment location T, the handheld microcurrent device 102 enters a treatment mode.

In one embodiment, the handheld microcurrent device 102 detects treatment locations T by detecting an impedance between the treatment electrode 108 and the return electrode 110. Treatment locations T are characterized by a lower impedance than surrounding areas due to enhanced conductivity of nerves.

According to an embodiment, in the treatment mode, the handheld microcurrent device 102 provides treatment stimulation to the treatment location T, corresponding to the nerve that is located during the detection mode. The handheld microcurrent device 102 may provide treatment stimulation to the treatment location T by providing electrical stimulation to the treatment location T that may affect the maxillary and/or mandibular nerve in such a way that the user experiences relief from troubling TMJ symptoms such as pain, inflammation, reduced movement, or other unpleasant symptoms.

According to an embodiment, the handheld microcurrent device 102 is a transcutaneous electrical nerve stimulation (TENS) device. The handheld microcurrent device 102 applies electrical treatment stimulation in the form of a stimulation current having selected characteristics. The stimulation current may have an average magnitude that is multiple orders of magnitude lower than common TENS devices. According to an embodiment, the stimulation current does not have a DC component, but is characterized by current spikes of alternating polarity. According to an embodiment, the treatment stimulation is provided at each treatment location T for a period of time between 2-30 seconds.

According to an embodiment, the handheld microcurrent device 102 applies the stimulation current by applying a stimulation voltage between the treatment electrode 108 and the return electrode 110.

According to an embodiment, the treatment electrode 108 is the active electrode of a monopolar design. The housing/device body 106 of the handheld microcurrent device 102 may serve as the return electrode 110 when return electrodes 110 are integrated into the device body 106. A user's hand holding the handheld microcurrent device 102 completes the electrical path from the treatment electrode 108 to the return electrode(s) 110 in that currents may travel from the treatment electrode 108, through at least a portion of the maxillary and/or mandibular nerve of the user and down to the hand of the user that is contacting the return electrode(s) 110, in an embodiment. The current may be referred to as stimulation current in this disclosure.

According to an embodiment, in the detection mode, the user presses the treatment electrode 108 to the skin and the handheld microcurrent device 102 initiates a low-frequency circuit that is maintained at a constant current. The handheld microcurrent device 102 may use the current to calculate the impedance in the path between the tissue at the treatment electrode 108 and the hand in contact with the handheld microcurrent device 102. The handheld microcurrent device 102 remains in the detection mode until the detection current indicates that the impedance is below a threshold impedance. The position of the treatment electrode 108 when the impedance is below the threshold impedance corresponds to a treatment area T. The treatment area T corresponds to a maxillary or mandibular nerve node area. When the handheld microcurrent device 102 identifies a treatment area T based on the calculated impedance, the handheld microcurrent device 102 enters the treatment mode. Entering the treatment mode may include outputting a signal to the user that the handheld microcurrent device 102 has triggered the start to the treatment mode. In an embodiment, the handheld microcurrent device 102 may initiate delivering treatment stimulation. In another embodiment, the handheld microcurrent device 102 may continue to output the microcurrent waveform used during the detection mode, and the signal to the user may indicate that the handheld microcurrent device has identified a treatment area T.

According to an embodiment, the handheld microcurrent device 102 may indicate to the user that the handheld microcurrent device 102 is in the treatment mode and that the user should hold the treatment electrode 108 at the treatment location T for a selected period of time. According to an embodiment, the handheld microcurrent device 102 may indicate the transition between the detection mode and the treatment mode by the indicators 114. The indicators 114 may include one or more LEDs that may provide an illumination schema that indicates whether the handheld microcurrent device 102 is in the detection mode or the treatment mode. According to an embodiment, the handheld microcurrent device 102 may indicate that the handheld microcurrent device 102 is in the treatment mode via haptic feedback (vibration). According to an embodiment, the handheld microcurrent device 102 may indicate whether the handheld microcurrent device 102 is in the detection mode, the treatment mode, or transitioning between the detection and the treatment modes by a combination of haptic feedback and the LED indicators 114. According to an embodiment, when the handheld microcurrent device 102 enters the treatment mode as indicated by one or more of the LED indicators 114 and haptic feedback, the user holds the handheld microcurrent device 102 in place until the treatment period has passed as indicated by cessation of haptic feedback and the LED indicators 114 (approximately 8-16 seconds in one example).

According to an embodiment, once the treatment period ends, the handheld microcurrent device 102 resets to detection mode. The user then may continue to glide the handheld microcurrent device 102 along the skin surface until reaching a next treatment area T, as identified based on impedance calculations. The user may adjust the impedance sensitivity of the handheld microcurrent device 102, in one embodiment. Changes in sensitivity adjust the impedance threshold at which the handheld microcurrent device 102 will enter treatment mode. According to an embodiment, changes in sensitivity do not change the output current. In another embodiment, a change in sensitivity may additionally change output current, for example during the detection mode and/or during the treatment mode.

In one embodiment of a treatment circuit of the disclosed handheld microcurrent device 102, a constant current stimulation output is between 1 Hertz and 1000 Hertz, bi-phasic, with no DC component signal, with an average current less than 300 microamps over a resistive load of 100-100 KΩ. The signal is presented to the treatment location by means of the treatment electrode 108, in one embodiment. According to an embodiment, a spring-loaded treatment electrode 108 activates the circuit and gently ramps the current to provide maximal comfort to the user.

According to an embodiment, constant current stimulation circuit output is directed to the treatment electrode 108 and returned to the circuit by way of the return electrode 110 (metallized portions of the device body 106). When the circuit is completed by the user pressing the device treatment electrode 108 to the face, a microcontroller monitors the resulting stimulation current and controls the stimulation voltage (across the treatment electrode 108 and the return electrode 110) to maintain the desired current, in one embodiment. The impedance of the circuit is then calculated and monitored by the microcontroller. In the event that the impedance falls below a specified threshold, which is indicative of a treatment location T, the microcontroller presents a treatment prompt through a user interface (UI), in one embodiment. According to an embodiment, the user is instructed to maintain the treatment electrode 108 location until the treatment prompt has timed out. After treatment time out, the user is instructed to slowly move the treatment electrode 108 to the next detected treatment location T, in one embodiment.

According to an embodiment, the sensitivity level setting determines the impedance threshold at which the handheld microcurrent device 102 will signal the user to detection of a treatment location T. The treatment sensitivity threshold may be increased to compensate for higher impedance associated with dry skin or the presence of makeup, in one embodiment. Upon detection of a treatment location T, the haptic motor starts to vibrate and the sensitivity level indicator LEDs 114 flash for a pre-programmed period of time, in one embodiment. Optionally, if the calculated impedance increases above the threshold (as when the treatment electrode 108 is removed from the face or moved to a higher impedance location on the face), the treatment session may be terminated by halting the output of the treatment mode signal(s) to the user.

In one embodiment, the handheld microcurrent device 102 is used as a handheld microcurrent TENS device used for the temporary relief of TMJ pain. The handheld microcurrent device 102 uses an average stimulation current that is several orders of magnitude smaller than that of previously cleared TENS devices, in one embodiment. In one embodiment, the handheld microcurrent device 102 is a microcurrent device designed to provide transcutaneous nerve stimulation to the regional areas associated with the maxillary and/or mandibular nerve, and particularly to areas of the maxillary and/or mandibular nerve in communication with nerves peripheral to the temporomandibular joint. Current levels are attuned to be appropriate for treatment of TMJ disorders.

The microcurrent device 102 is held in the hand, with the treatment electrode 108 of the handheld microcurrent device 102 applied to the skin superjacent to selected portions of the maxillary and/or mandibular nerve. In one embodiment, the treatment electrode 108 is an active electrode of a monopolar design. The housing/device body 106 of the handheld microcurrent device 102 may serve as the return electrode 110 when return electrodes 110 are integrated into the device body 106. A user's hand holding the microcurrent device 102 completes the electrical path from the treatment electrode 108 to the return electrode(s) 110 in that stimulation currents may travel between the treatment electrode 108 and the return electrode 110 through the maxillary and/or mandibular nerve. The stimulation current may be passed in either polarity between the treatment electrode 108 and the return electrode 110 through the body of the user, according to an embodiment. The stimulation current may alternate polarity during the treatment mode, according to an embodiment.

In one embodiment, when the user turns the handheld microcurrent device 102 "ON" and presses the treatment electrode 108 to the skin, the handheld microcurrent device 102 initiates a low-frequency circuit that is maintained at a constant detection current. The handheld microcurrent device 102 may use the detection current to calculate the impedance in the path between the tissue at the treatment electrode 108 and the hand in contact with the handheld microcurrent device 102. In one embodiment, if the calculated impedance is above an impedance threshold, the handheld microcurrent device 102 is in "detection" mode. Conversely, in one embodiment, when the impedance falls below the impedance threshold, the handheld microcurrent device 102 enters a "treatment" mode. In one embodiment, in the treatment mode the stimulation current is has a greater magnitude than the current used in the detection mode. In another embodiment, the pulse period (the time between individual pulses) is shorter than the pulse period used in the detection mode.

In one embodiment, the user is instructed to glide the treatment electrode 108 of the handheld microcurrent device 102 along the skin. The switch (transition) from detection mode to the treatment mode is signaled to the user via haptic (vibration) feedback and blinking of the indicator LEDs 114, in one embodiment. The user then holds the handheld microcurrent device 102 in place until the treatment period has passed as indicated by cessation of haptic and LED indicators 114 (approximately 8 seconds, in one example), in one embodiment.

In one embodiment, once the treatment period ends, the handheld microcurrent device 102 resets to detection mode. The user then may continue to glide the handheld microcurrent device 102 along the indicated path until reaching the next low-impedance area. The user may adjust the impedance sensitivity of the handheld microcurrent device 102, in one embodiment. Changes in sensitivity adjust the impedance threshold at which the handheld microcurrent device 102 will enter treatment mode. Changes in sensitivity do not change the stimulation current, in one embodiment. In another embodiment, the sensitivity selector is used to change stimulation current to meet a personal preference of the user.

In one embodiment, the sensitivity setting button 116 may allow a user to toggle through different sensitivity levels that may be indicated by, for example, three indicator LEDs 114, as shown in FIGS. 1A-1C. In one embodiment, an overcoat/insulator may cover the device body 106 of the handheld microcurrent device 102 except for where the return electrode 110 is exposed to contact with the skin of the user's hand to provide an electrical path.

In one embodiment, the treatment electrode 108 includes an elastomeric material intended to minimize point pressure against the skin of the user. Various elastomers including silicone, fluorine-substituted silicones, natural rubber, vulcanized rubber, latex, latex derivatives, etc. may be used alone or in combination to form a support structure of the treatment electrode 108. In another embodiment, a non-elastomeric dielectric material such as a polymer, polymer combination, or glass may be used alone or in combination to form the support structure of the active electrode. The support structure may be formed to have a relatively low thermal conductivity and/or may have a smooth radius to reduce point pressure against the skin of the user. Various conductive fibers or particles such as gold, silver, stainless steel, carbon fiber, carbon nanotubes, and/or alternating bond length (electron-conjugated) polymers are contemplated as current carriers supported by a dielectric support structure.

In one embodiment, the handheld microcurrent device 102 includes a spring-loaded treatment electrode 108 and the treatment electrode 108 is a small surface area metalized feature (tip) of the device body 106 that is applied to the treatment regions of the face. In one embodiment, a micro-switch initiates the therapy circuit when the treatment electrode 108 is depressed. The handheld microcurrent device 102 may include a microprocessor microcontroller, a battery, and a transformer/voltage step-up circuit. In one embodiment, the return electrode 110 is a large surface area metalized region of the device body 106 that is in contact with the user's hand.

In one embodiment, the user interface of the handheld microcurrent device 102 includes an LED treatment indicator 114 (e.g., LEDs 114), a sensitivity level adjustment button 116, and a haptic feedback circuit. The LED sensitivity level indicates selected sensitivity levels in addition to low battery and charge status, an on/off button with integrated LED(s) to indicate "on" or "off" state, and a haptic feedback circuit.

In one embodiment, the handheld microcurrent device 102 includes an overcoat that is electrically insulated. The overcoat may cover a portion of the metalized return electrode 110 so long as a portion (e.g., 10%) of the return electrode 110 is exposed. In one embodiment, the handheld microcurrent device 102 includes a battery charging port 112 and circuit to charge an internal battery.

As described above, the handheld microcurrent device 102 may be used as a TENS device that applies microamp electrical stimulation to nerves and vasculature near the TMJ area.

FIG. 3 illustrates nerves that the handheld microcurrent device 102 may be applied to by a user to facilitate treatment/therapy.

In one embodiment of a treatment circuit of the disclosed handheld microcurrent device 102, the constant current stimulation output is approximately 1 Hertz-1000 Hertz, bi-phasic, no DC component signal with an average current of less than 300 microamps over a resistive load of 100-100 K $\Omega$. The signal is presented to the user by means of the monopolar electrode, in one embodiment. In one embodiment, the spring-loaded treatment electrode 108 activates the circuit and gently ramps the current to provide maximal comfort to the user.

In one embodiment, constant current stimulation circuit output is directed to the treatment electrode 108 (the device tip 108) and returned to the circuit by way of the return electrode 110 (metallized portions of the device body 106). When the circuit is completed by the user pressing the device treatment electrode 108 to the face, a microcontroller monitors the resulting stimulation current and controls the stimulation voltage (across the treatment electrode 108 and return electrode 110) to maintain the desired current, in one embodiment.

The impedance of the circuit is then calculated and monitored by the microcontroller. In the event that the impedance falls below a specified threshold, which is indicative of a treatment location T, the microcontroller presents a treatment prompt through the user interface (UI), in one embodiment. In one embodiment, the user is instructed to maintain the treatment electrode 108 location until the treatment prompt has timed out. After treatment time out, the user is instructed to slowly move the treatment electrode 108 to the next detected treatment location T, in one embodiment.

In one embodiment, the sensitivity level setting determines the impedance threshold at which the handheld microcurrent device 102 will signal the user to detection of a treatment location T. The treatment sensitivity threshold may be increased to compensate for higher impedance associated with dry skin or the presence of makeup, in one embodiment. Upon detection of a treatment location T, the haptic motor starts to vibrate and the sensitivity level indicator LEDs 116 flash for a pre-programmed period of time, in one embodiment. If the calculated impedance increases above the threshold (treatment electrode 108 removed from the face or moved to a higher impedance location on the face), the treatment session may be terminated.

Figure 4:
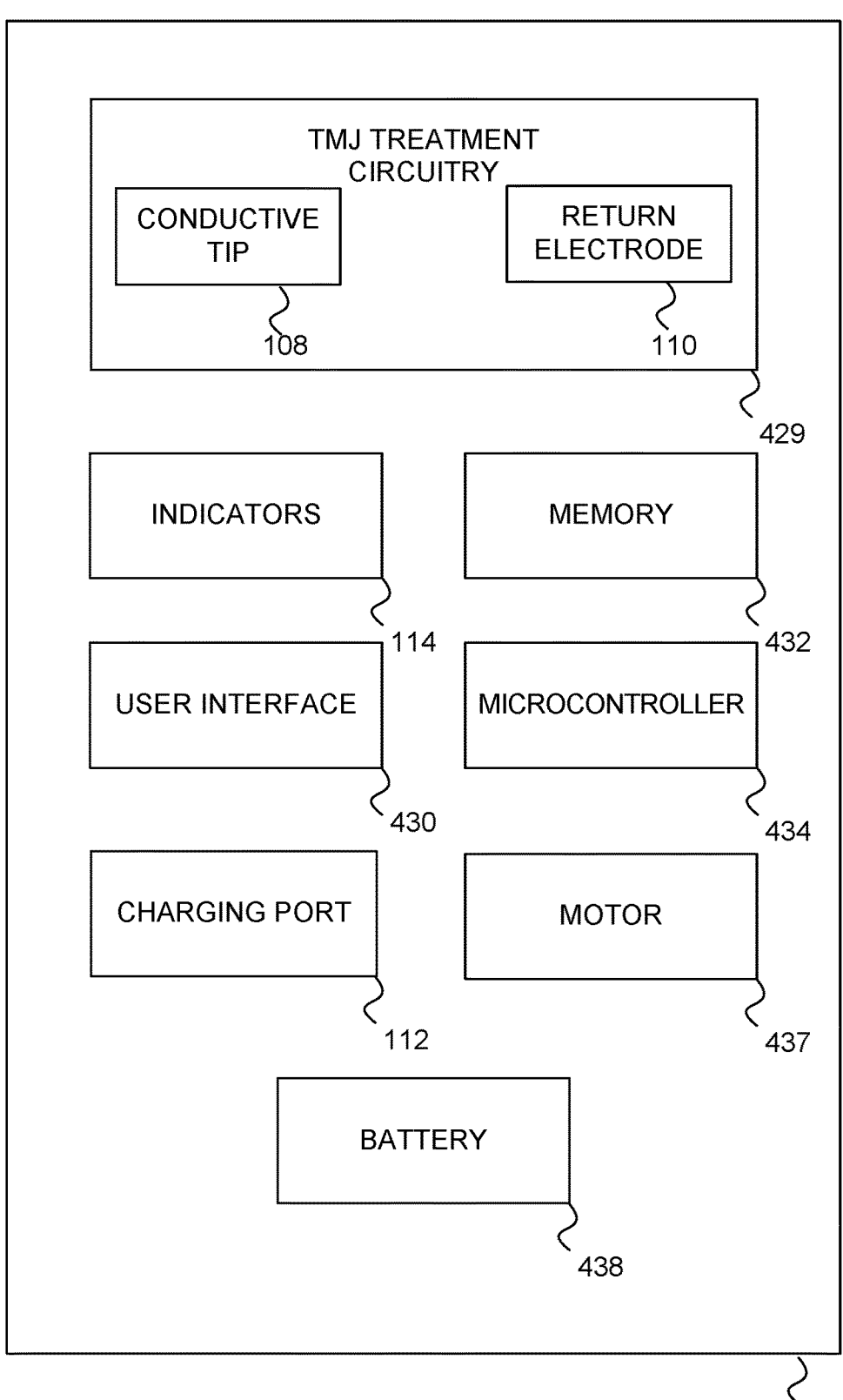
FIG. 4 is a block diagram of a microcurrent device, according to an embodiment of the disclosure.

FIG. 4 is a block diagram of the handheld microcurrent device 102, according to an embodiment. The handheld microcurrent device 102 includes a TMJ treatment circuitry (also referenced as current output circuit) 429, the charging port 112, the indicators 114, a user interface 430, a memory 432, a microcontroller 434, a motor 437, and a battery 438. The current output circuit 429 includes the treatment electrode 108 and the return electrode 110. The handheld microcurrent device 102 utilizes these components to provide effective treatments to the user.

According to an embodiment, the treatment electrode 108 and the return electrode 110 cooperate together to provide both detection currents and treatment stimulation. Detection and treatment currents are passed between the treatment electrode 108 and the return electrode 110 through the body of the user. In particular, the treatment electrode 108 is positioned in contact with the user's skin to the maxillary and/or mandibular nerve areas of the user. The return electrode 110 is in contact with the user's hand as the user holds the handheld microcurrent device 102. The detection and treatment currents pass between the treatment electrode 108 and the return electrode 110 via the hand, body, and facial skin of the user.

According to an embodiment, the indicators 114 provide indications to the user as to the current mode of operation of the handheld microcurrent device 102. The indicators 114 may include one or more LEDs that may be illuminated in selected ways to indicate whether the handheld microcurrent device 102 is powered on, whether the handheld microcurrent device 102 is in a treatment mode, whether the handheld microcurrent device 102 is in a detection mode, whether the handheld microcurrent device 102 awaits user input, whether the handheld microcurrent device 102 is communicating with a personal electronic device, or indications of other types of functionality of the handheld microcurrent device 102. According to an embodiment, the indicators 114 may include a display capable of outputting text or images to indicate to the user the various functions of the handheld microcurrent device 102.

According to an embodiment, the user interface 430 includes various components that enable the user to control functionality of the handheld microcurrent device 102. The user interface 430 may include the power on-off button 118, the sensitivity setting button 116, or other kinds of buttons, switches, touchscreens, or input controls that enable the user to control functionality of the handheld microcurrent device 102. The user may manipulate the user interface 430 in order to control the functionality of the handheld microcurrent device 102.

According to an embodiment, the memory 432 stores data related to the functionality of the handheld microcurrent device 102. The memory 432 may include software instructions by which the various functionalities of the handheld microcurrent device 102 may be implemented. The memory 432 may include reference impedance values and/or threshold impedance values. The reference and threshold impedance values may be utilized in the detection mode of the handheld microcurrent device 102. The memory 432 may include data indicating previously detected treatment locations T. The memory 432 may include other settings such as treatment lengths, treatment stimulation strengths, frequencies of treatments, or other settings including default settings and user selected settings for operation of the handheld microcurrent device 102. The memory 432 may include one or more of EEPROMs, flash memory, ROMs, SRAM, DRAM, or other kinds of computer readable media capable of storing instructions that may be executed by the microcontroller 434.

According to an embodiment, the motor 437 enables the handheld microcurrent device 102 to provide haptic feedback to the user. For example, during a treatment mode in which the handheld microcurrent device 102 provides stimulation treatment to a treatment area T, the motor 437 may cause the handheld microcurrent device 102 to vibrate mildly to indicate to the user that the handheld microcurrent device 102 is in the treatment mode. The motor 437 may cease the vibration to indicate that the handheld microcurrent device 102 is no longer in the treatment mode. The motor 437 may generate vibrations to provide a variety of types of indications to the user of the handheld microcurrent device 102.

According to an embodiment, the battery 438 provides power to the handheld microcurrent device 102. The battery 438 may include a rechargeable battery 438 that enables the user to recharge the battery 438 after the battery 438 has become depleted through use. The battery 438 may be a lithium-ion battery, a NiCad battery, a carbon zinc battery, an alkaline battery, a nickel metal hydride battery, or other types of batteries.

According to an embodiment, the charging port 112 enables the user to recharge the battery 438. For example, the charging port 112 may be configured to receive a charging cable that connects the charging port 112 to a power source. The charging port 112 may include a micro USB port, a USB 2.0 port, a USB 3.0 port, a USB C port, or other types of charging ports. According to an embodiment, the charging port 112 enables charging and data transmission. When a charging cable is plugged into the charging port 112, the battery 438 may be charged and data may be received or transmitted over the charging cable via the charging port 112. According to an embodiment, the handheld microcurrent device 102 may operate while a charging cable is attached to the charging port 112. Thus, if the battery 438 is depleted, the user may attach a charging cable to the charging port 112 and may operate the handheld microcurrent device 102 from power received via the charging port 112.

According to an embodiment, the microcontroller 434 controls the functionality of the other components of the handheld microcurrent device 102. The microcontroller 434 is communicatively coupled to the treatment electrode 108, the return electrode 110, the indicators 114, the memory 432, the user interface 430, and the charging port 112.

According to an embodiment, the microcontroller 434 executes the software instructions stored in the memory 432 to implement the various modes of functionalities of the handheld microcurrent device 102. The microcontroller 434 causes the treatment electrode 108 and the return electrode 110 to pass the detection currents in the detection mode, and to pass the treatment stimulation currents in the treatment mode. The microcontroller 434 controls the indicators 114 to indicate the various modes of functionalities of the handheld microcurrent device 102. The microcontroller 434 communicates with the user interface 430 to enable the user to select various modes of operation of the handheld microcurrent device 102.

Figure 5:
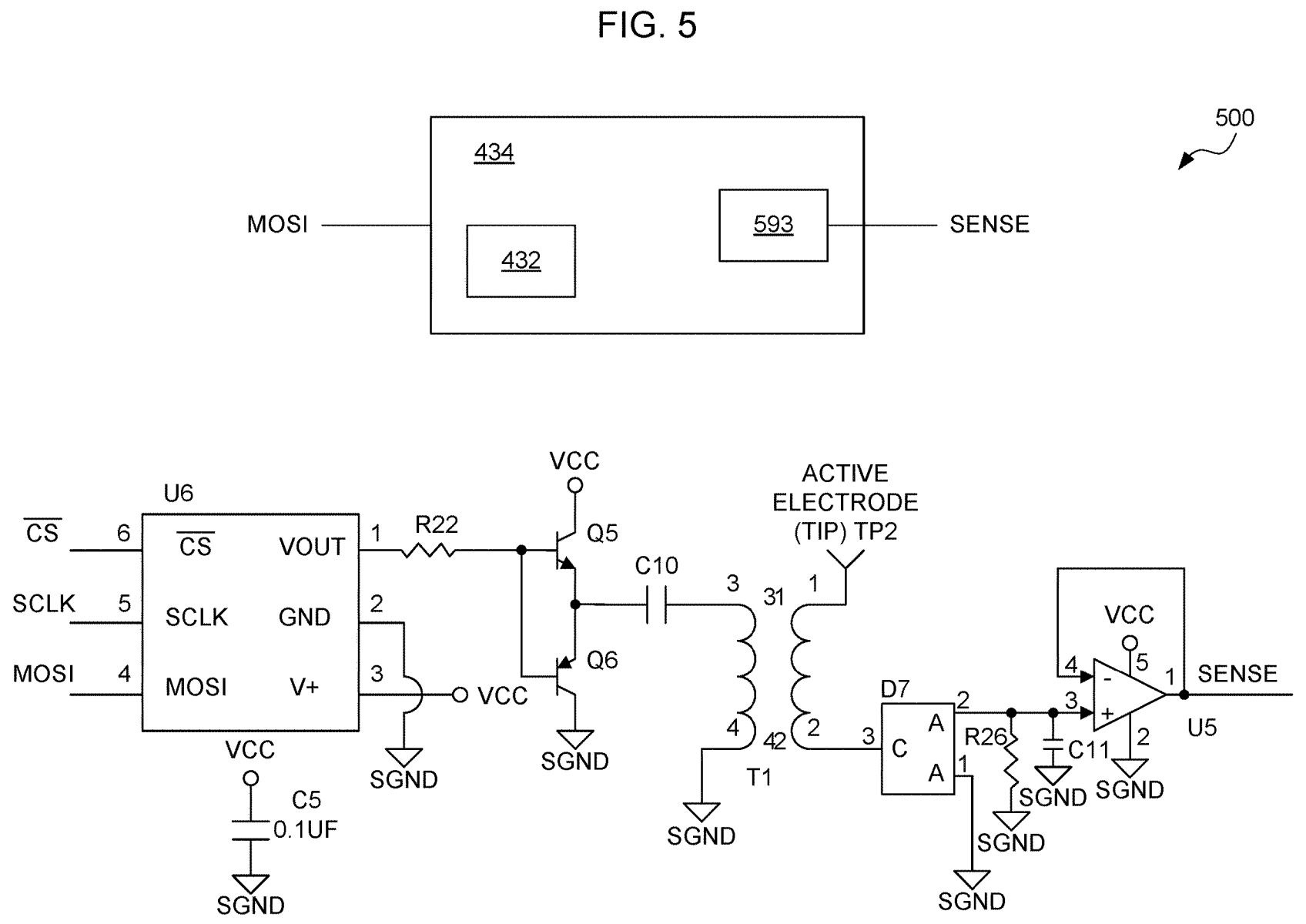

FIG. 5 illustrates an example TMJ treatment circuitry 500 for use with the handheld microcurrent device 102, according to an embodiment of the disclosure. The TMJ treatment circuitry 500 is positioned within the housing/device body 106, according to one embodiment. The TMJ treatment circuitry 500 includes a microcontroller 434 including a memory 432 and an analog-to-digital converter (ADC) 593. In the illustrated embodiment of FIG. 5, the TMJ treatment circuitry 500 also includes a stimulation driver stage and a peak detector.

In one embodiment, the stimulation driver stage is coupled to apply a stimulation voltage between the treatment electrode (active electrode TP2) and the return electrode 110 (not illustrated in FIG. 5). In the illustrated embodiment, the stimulation driver stage includes a digital-to-analog converter (DAC), an amplifier, a transformer, and a capacitor. In one embodiment, the DAC (U6) is coupled to generate an analog voltage (pin 1 of U6, VOUT) in response to a digital instruction from the microcontroller 434 received via the MOSI (Master Out Slave In) communication channel of pin 4 of U6.

In the illustrated embodiment, the amplifier includes transistors Q5 and Q6 and is coupled to generate an amplified analog voltage (emitter node of Q5) in response to receiving the analog voltage from the DAC (U6).

In the illustrated embodiment, the transformer T1 includes a primary side (nodes 3 and 4) and a secondary side (nodes 1 and 2). The treatment electrode (active electrode TP2) is coupled to node 1 of the secondary side of the transformer T1, in the illustrated embodiment.

In the illustrated embodiment, capacitor C10 is coupled between the amplifier and a primary side of the transformer T1 to block the DC (direct current) portions of the amplified analog signal.

In one embodiment, the peak detector includes a diode element, a buffer circuit, and a sample and hold circuit. In the illustrated embodiment, the diode element is D7. In one embodiment, the buffer circuit is coupled to output a peak stimulation current signal. In one embodiment, the peak detector is coupled to generate a peak stimulation current signal on the node 1 output of op-amp U5 in response to receiving a stimulation signal from the treatment electrode. In the illustrated embodiment, the stimulation signal may travel from the treatment electrode TP2 to node 2 of the transformer T1 via node 1 of the transformer T1.

In one embodiment, the sample and hold circuit is coupled between the diode element D7 and the buffer circuit and the diode element is coupled between the secondary side of the transformer and the sample and hold circuit. In the illustrated embodiment, the sample and hold circuit includes resistors R26 and capacitor C11.

In one embodiment, the microcontroller 434 is coupled to receive the peak stimulation current signal (SENSE) from the peak detector and coupled to the stimulation driver stage for adjusting the stimulation voltage in response to the peak stimulation current signal. In one embodiment, the microcontroller 434 dynamically adjusts the stimulation voltage to keep the peak stimulation current signal at a constant value. In one embodiment, microcontroller 434 includes ADC 593 coupled to sample the peak stimulation current signal and drive the digital instruction to the DAC (via MOSI communication channel) to keep the peak stimulation current signal at the constant value.

The TMJ treatment circuitry 500 of FIG. 5 provides a means to maintain a nearly constant (and comfortable) stimulation current in response to varying resistance or impedance. Turning to a more specific description of an embodiment of TMJ treatment circuitry 500, a digital-to-analog converter (DAC) U6 receives commands from the microcontroller 434 to generate a square wave with a variable amplitude of 0 to +Vcc volts. The DAC output is current limited by R22 and is used to drive a push-pull output power stage comprised of Q5 and Q6, in the illustrated embodiment. The output of the push-pull stage is AC coupled by C10 and drives the primary side of a step-up transformer T1. C10 blocks the DC component of the square wave and allows through only the rising and falling edges of the square wave. The transformer converts the high current, low voltage edge input to the high voltage, low (microcurrent) stimulation current output, in the illustrated embodiment.

One end of the secondary side of the transformer is connected to the treatment electrode. The other end of the secondary coil is connected to a dual diode array D7. The diode array acts as the stimulation current positive peak detector. R26 and C11 provide a simple sample and hold function of the detected peak. The peak detector output is buffered by op-amp U5. The output of the op-amp is then sampled by the ADC of the microcontroller.

During use, a control loop is formed by the DAC, peak detector, and the microcontroller ADC. The sensed positive peaks of the stimulation current are maintained at a constant level by controlling the DAC output. As the total resistance decreases, the control loop reduces the DAC output which reduces the amplitude of the edges being input to the transformer. The control loop effectively converts the voltage source output of the transformer to a constant current source, in the illustrated embodiment. In this manner, any uncomfortable surges in current are reduced during treatment.

Figure 6:
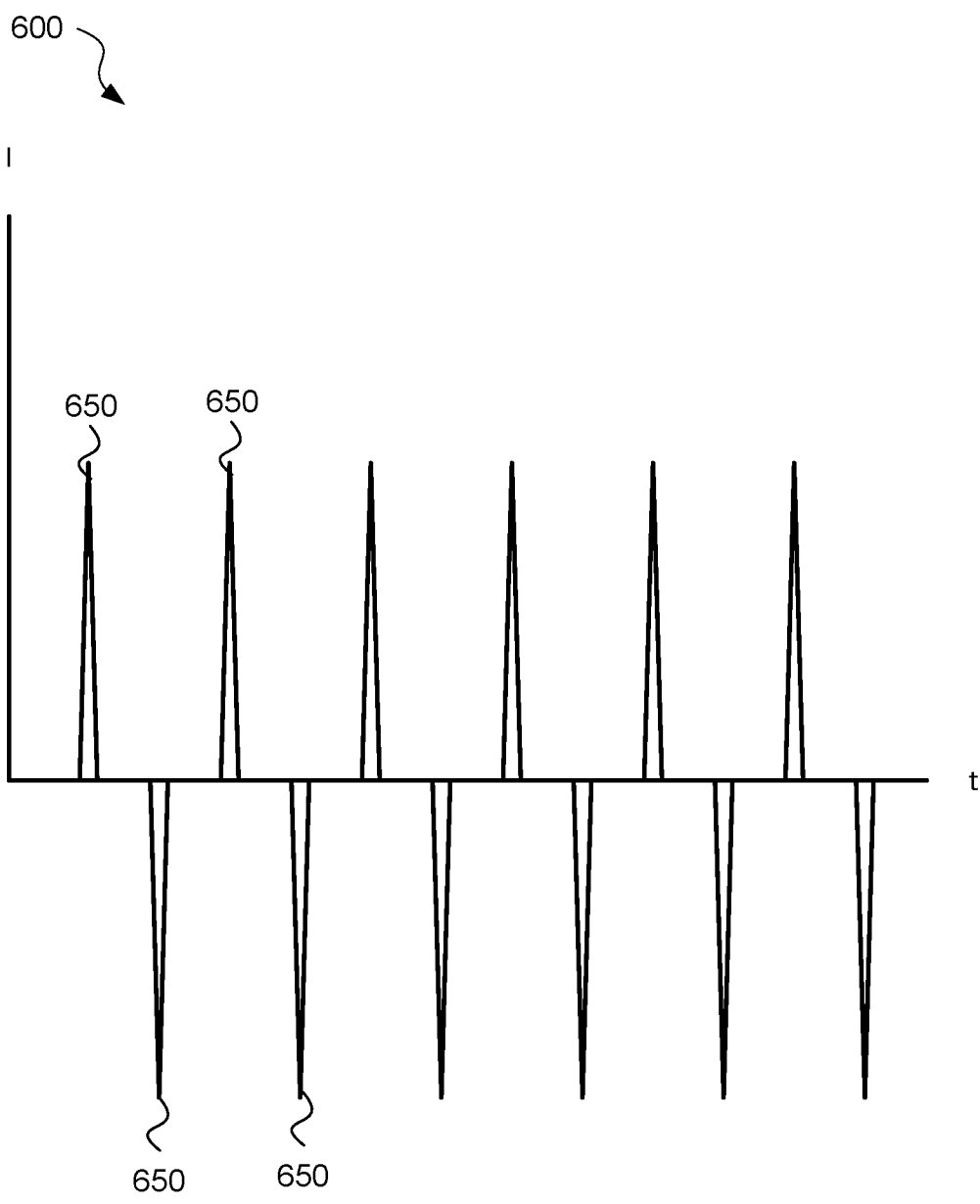
FIG. 6 is a waveform corresponding to treatment current vs. time, according to an embodiment of the disclosure.

FIG. 6 is a graph 600 of a treatment stimulation current (I) vs time (t), according to an embodiment. The treatment stimulation current is applied during a treatment mode of the handheld microcurrent device 102 after the handheld microcurrent device 102 has identified a treatment location T. The treatment stimulation current provides relief to TMJ symptoms experienced by the user.

According to an embodiment, the treatment stimulation current corresponds to a series of sharp current spikes 650 or peaks. According to an embodiment, successive current spikes 650 alternate in polarity such that every other current spike 650 flows in a first direction, while intervening current spikes 650 flow in a second, opposite, direction.

According to an embodiment, the current spikes 650 correspond to the rising and falling edges of a square wave voltage signal. In one embodiment, the treatment stimulation current is generated by feeding a square wave voltage signal to a transformer, such as the transformer T1, via a capacitor, such as the capacitor C10. Those of skill in the art will recognize, in light of the present disclosure, that a treatment stimulation current in accordance with FIG. 6 may be generated in various ways. All such other ways for generating the treatment stimulation current fall within the scope of the present disclosure.

In one embodiment, the treatment stimulation current has no DC offset. The lack of a DC offset may enhance the therapeutic effect of the treatment stimulation current. This is because, in one interpretation, the rapid changes in current magnitude and polarity promote physiological effects that do not occur in the presence of a DC current.

In one embodiment, the TMJ treatment circuitry 429, including the microcontroller 434 and the memory 432, adjust the stimulation voltage between the treatment electrode and the return electrode to maintain a constant treatment stimulation current during the treatment mode. In one embodiment, maintaining a constant treatment stimulation current corresponds to causing the peaks of the treatment stimulation current to have substantially the same magnitudes. In one embodiment, maintaining a constant treatment stimulation current corresponds to causing the peaks of the treatment stimulation current to have substantially the same absolute values. Thus, the positive current peaks and the negative current peaks have the same absolute value, in one embodiment. Alternatively, maintaining a constant treatment stimulation current corresponds to causing the positive current peaks to have a same first magnitude, and causing the negative current peaks to have a same second magnitude.

In one embodiment, the peaks of the TMJ treatment stimulation current have a magnitude of less than or equal to 15 milliamps. In one embodiment, the peaks of the treatment stimulation current have a magnitude greater than or equal to 3 milliamps. In one embodiment, the peaks of the treatment stimulation current have a magnitude of about 6 milliamps. In one embodiment, the TMJ treatment stimulation current spikes 650 have an average current less than or equal to 300 microamps. In one embodiment, the TMJ treatment stimulation current spikes 650 have an average current greater than 60 microamps.

In one embodiment, the frequency of the treatment stimulation current is less than 1000 Hertz. In one embodiment, the period of a single treatment stimulation current cycle corresponds to the time between current peaks of the same polarity. In one embodiment, the frequency of the treatment stimulation current is between 1 Hertz and 100 Hertz. In one embodiment, the spikes 650 in the treatment stimulation current make up less than 10% of a single cycle. In one embodiment, the spikes 650 in the treatment stimulation current make up less than 5% of a single cycle. In one embodiment, the spikes 650 in the treatment stimulation current make up about 2% of a single cycle.

In one embodiment, during the treatment mode, the handheld microcurrent device 102 measures the impedance by measuring the peaks of the treatment stimulation current. In one embodiment, the handheld microcurrent device 102 adjusts a stimulation voltage applied between the treatment electrode 108 and the return electrode 110 to bring the magnitude of the peaks of the treatment stimulation current back to a desired constant value.

In one embodiment, in the detection mode in which the handheld microcurrent device 102 identifies treatment locations T, the handheld microcurrent device 102 measures the impedance by applying a detection current with a waveform similar or identical to the treatment stimulation current waveform and measuring the magnitude of the current peaks of the detection current in order to determine the impedance. In one embodiment, the handheld microcurrent device 102 measures the impedance by passing a detection current with a smaller magnitude than the treatment stimulation current. In one embodiment, during the detection mode, the handheld microcurrent device 102 applies a detection voltage that is lower than the stimulation voltage applied during the treatment mode. In one embodiment, the handheld microcurrent device 102 measures the impedance by passing a detection current with a waveform entirely different than the treatment stimulation current waveform.

Those of skill in the art will recognize, in light of the present disclosure, that in practice the treatment current may vary from the graph 600. For example, the risetime and fall time of a given current spike 650 may not be identical. The rise times and fall times of separate current spikes 650 may not be identical to each other. A given current spike 650 may include, at the tail end, a brief portion that flows in the opposite polarity to the primary polarity of the current spike 650. In a constant current situation, the current spikes 650 may have slightly differing magnitudes while remaining substantially the same. There may be noise present among the current waveform. All such variations from the graph 600 fall within the scope of the present disclosure.

In one embodiment, the current spikes 650 are sharp increases in current followed by a sharp drop in current. In one embodiment, the rise time and fall time of a current spike 650 makes up 90% or more of the current spike 650.

FIG. 7 is a flow chart illustrating an example process 700 of operating a handheld microcurrent device, according to an embodiment of the disclosure.

In process block 702, an impedance is detected between a treatment electrode 108 of the handheld microcurrent device 102 and a return electrode 110 of the handheld microcurrent device 102.

In process block 704, a treatment mode of the handheld microcurrent device 102 is initiated a stimulation voltage between the treatment electrode 108 and the return electrode 110 when the impedance drops below a threshold.

In process block 706, a stimulation voltage is adjusted as the impedance between the treatment electrode 108 and the return electrode 110 changes during the treatment mode.

In one embodiment, an initial stimulation voltage of the treatment mode driven across the treatment electrode 108 and the return electrode 110 is a personal stimulation voltage saved to therapy profile in a memory 432 of the handheld microcurrent device 102 and the personal stimulation voltage is based on a last stimulation voltage used by the handheld microcurrent device 102.

In one embodiment, an initial stimulation voltage of the treatment mode driven across the treatment electrode 108 and the return electrode 110 is a user selected stimulation voltage received from a user input of the handheld microcurrent device 102.

In one embodiment, the process 700 further includes initiating a haptic feedback of the handheld microcurrent device 102 when the treatment mode is initiated.

In one embodiment, the process 700 further includes illuminating a light emitting diode of the handheld microcurrent device 102 when the treatment mode is initiated.

In one embodiment, the return electrode 110 is attached with a device body 106 of the handheld microcurrent device 102 that is formed to be held by a hand of a user of the handheld microcurrent device 102 and the return electrode 110 is exposed to contact the hand of the user. In one embodiment, the return electrode 110 is included in a device body 106 of the handheld microcurrent device 102, and wherein the device body 106 includes conductive polycarbonate to serve as the return electrode 110.

In one embodiment, the process 700 further includes turning off the handheld microcurrent device 102 when the impedance between the treatment electrode 108 and the return electrode 110 is over a pre-determined threshold for a pre-determined time period (e.g., 2 minutes).

In one embodiment of the process 700, driving the stimulation voltage across the treatment electrode 108 and the return electrode 110 includes driving voltage pulses across the treatment electrode 108 and the return electrode 110.

In one embodiment, the treatment electrode 108 is a spring-loaded tip to reduce the pressure of the treatment electrode 108 on a skin area of the user of the handheld microcurrent device 102. In one embodiment, the treatment electrode 108 includes a conductor and a dielectric tip and both the conductor and the dielectric tip contact a skin area of the user when the treatment electrode 108 is applied to the skin area of the user. In one embodiment, the conductor includes carbon fiber.

In one embodiment, a method of operating a handheld microcurrent device 102 includes measuring a stimulation signal from a treatment electrode 108 of the handheld microcurrent device 102 where the stimulation signal is representative of a stimulation current between the treatment electrode 108 and a return electrode 110 attached with a device body 106 of the handheld microcurrent device 102. The process further includes dynamically adjusting a stimulation voltage across the treatment electrode 108 and the return electrode 110 to keep the stimulation current at a constant value in response to measuring the stimulation signal.

According to an embodiment, a method of operating a handheld microcurrent device 102 includes detecting an impedance between a treatment electrode 108 of the handheld microcurrent device 102 and a return electrode 110 of the handheld microcurrent device 102. The method includes initiating a treatment mode of the handheld microcurrent device 102 when the impedance drops below a threshold by outputting a signal to the user that the handheld microcurrent device 102 has triggered responsive to the impedance drop. The signal alerts the user to hold the treatment electrode at the present skin surface location until the treatment mode times out and the signal is no longer output. The method includes changing the stimulation voltage as the impedance between the treatment electrode 108 and the return electrode 110 changes during the treatment mode.

According to an embodiment, a method includes applying, with a handheld microcurrent device 102, TMJ treatment stimulation to a TMJ treatment location T superjacent to a maxillary and/or mandibular nerve of a user by applying a stimulation current between a treatment electrode 108 and a return electrode 110 of the handheld microcurrent device 102. The method includes measuring a stimulation signal representative of the stimulation current and maintaining a constant value of the stimulation current during treatment mode by dynamically adjusting a stimulation voltage between the treatment electrode 108 and the return electrode 110 in response to measuring the stimulation signal.

According to an embodiment, a method of operating a handheld microcurrent device 102 includes initiating a treatment mode of the handheld microcurrent device 102 by applying a stimulation voltage between a treatment electrode 108 of a handheld microcurrent device 102 and a return electrode 110 of the handheld microcurrent device 102. The method includes changing the stimulation voltage as an impedance between the treatment electrode 108 and the return electrode 110 changes during the treatment mode.

According to an embodiment, a handheld microcurrent device 102 includes a treatment electrode 108, a return electrode 110 operatively coupled to a device body 106 of the handheld microcurrent device 102, and a stimulation driver stage coupled to apply a stimulation voltage between the treatment electrode 108) and the return electrode 110. The handheld microcurrent device 102 includes a peak detector coupled to generate a peak stimulation current signal in response to receiving a stimulation signal from the treatment electrode 108. The handheld microcurrent device 102 includes a microcontroller 434 coupled to receive the peak stimulation current signal from the peak detector and coupled to the stimulation driver stage for adjusting the stimulation voltage in response to the peak stimulation current signal. The microcontroller 434 dynamically adjusts the stimulation voltage to keep the peak stimulation current signal at a constant value.

According to an embodiment, a handheld microcurrent device 102 includes a housing 106 configured to be held in a hand of user, a treatment electrode 108 coupled to the housing 106, and a return electrode 110 positioned on the housing 110 such that when a user holds the housing 106 the hand of the user is in contact with the return electrode 110. The handheld microcurrent device 102 includes TMJ treatment circuitry 429, 500 positioned within the housing 106 and configured to detect an impedance between the treatment electrode 108 and the return electrode 110 and to enter a treatment mode responsive to the impedance dropping below a threshold by applying a stimulation current between the treatment electrode 108 and the return electrode 110.

According to an embodiment, a method includes detecting, during a detection mode, an impedance between a treatment electrode 108 of a microcurrent device 102 and a return electrode 110 of the microcurrent device 102. The method includes initiating a treatment mode of the microcurrent device 102 when the impedance drops below a threshold including passing a treatment stimulation current between the treatment electrode 108 and the return electrode 110. The treatment stimulation current includes a series of current spikes 650. According to an embodiment, the method includes generating the current spikes corresponding to rising and falling edges of a square wave voltage signal, with attenuation of the respective top and bottom of the square wave.

According to an embodiment, a method includes detecting, during a detection mode, an impedance between a treatment electrode 108 of the microcurrent device 102 and a return electrode 110 of the microcurrent device 102. The method includes initiating a treatment mode of the microcurrent device 102 when the impedance drops below a threshold including passing a treatment stimulation current between the treatment electrode 108 and the return electrode 110. The treatment stimulation current has an average magnitude of greater than microamps and less than 300 microamps.

According to an embodiment, a method includes initiating a treatment mode of a microcurrent device 102 and passing, during the treatment mode of the microcurrent device 102, a treatment stimulation current between a treatment electrode 108 of the microcurrent device 102 and a return electrode 110 of the microcurrent device 102. The treatment stimulation current has an average magnitude of less than 300 microamps.

According to an embodiment, a method includes initiating a treatment mode of a microcurrent device 102 and passing, during the treatment mode of the microcurrent device 102, a treatment stimulation current between a treatment electrode 108 of the microcurrent device 102 and a return electrode 110 of the microcurrent device 102, wherein the treatment stimulation current includes a series of current spikes 650 with a frequency less than 1000 Hertz and an average magnitude of less than 300 microamps.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A method for treating human temporomandibular joint (TMJ) symptoms, comprising:

passing a treatment stimulation current, including passing a series of current spikes, between a treatment electrode in contact with a skin surface of a user in a position corresponding to a predetermined TMJ treatment location and a return electrode of a microcurrent device in contact with a hand of the user;

detecting an impedance between the treatment electrode and the return electrode; and maintaining a peak value of the current spikes at 15 milliamps or less by adjusting a stimulation voltage as the impedance between the treatment electrode and the return electrode changes.

2. The method of claim 1, wherein adjusting the stimulation voltage includes maintaining a substantially constant treatment current by adjusting the stimulation voltage responsive to changes in the impedance.

3. The method of claim 2, wherein maintaining a substantially constant treatment current includes maintaining peaks of the series of current spikes at a substantially constant value.

4. The method of claim 1, wherein passing the series of current spikes includes passing a series of current spikes having a peak magnitude of greater than 3 milliamps.

5. The method of claim 1, wherein passing the series of current spikes includes passing a series of current spikes having a time-averaged value of less than about 300 milliamps.

6. The method of claim 1, wherein passing the series of current spikes includes passing a series of current spikes having a time-averaged value of about 120 microamps.

7. The method of claim 1, further comprising alternating a polarity of the current spikes.

8. The method of claim 1, wherein passing the treatment stimulation current includes passing the treatment stimulation current at a frequency of between 1 Hertz and 100 Hertz.

9. The method of claim 1, wherein passing the treatment stimulation current includes passing the treatment stimulation current with a zero DC offset.

10. The method of claim 1, wherein passing the series of current spikes includes passing a series of current spikes with a duty cycle of less than 5%.

11. The method of claim 1, further comprising generating the series of current spikes corresponding to rising and falling edges of a square wave voltage signal, with attenuation of the respective top and bottom of the square wave.

12. A treatment method for treating human temporomandibular joint (TMJ) symptoms, comprising:

grasping a microcurrent TMJ treatment device, the surface of the microcurrent TMJ treatment device supporting a return electrode, such that grasping the microcurrent TMJ treatment device makes an electrical coupling between a user's hand and the return electrode;

holding the microcurrent TMJ treatment device with a treatment electrode of the microcurrent TMJ treatment device in contact with a first skin surface location, the first skin surface location of the user corresponding to a predetermined treatment location for affecting TMJ symptoms; and maintaining contact between the treatment electrode and the first skin surface location while the treatment electrode and return electrode of the microcurrent TMJ treatment device pass a biphasic waveform through a portion of the user's body including tissues subjacent the treatment electrode, and through the shoulder, arm, and hand, while the microcurrent TMJ treatment device maintains the biphasic waveform at a constant peak current level of 15 milliamps or less.

13. The treatment method of claim 12, wherein the predetermined treatment location is superjacent to a maxillary nerve of the user.

14. The treatment method of claim 12, wherein the predetermined treatment location includes each of a plurality of predetermined treatment locations over a maxillary nerve and/or over a mandibular nerve.

15. A treatment method for treating human temporomandibular joint (TMJ) symptoms, comprising:

grasping a microcurrent TMJ treatment device, the surface of the microcurrent TMJ treatment device supporting a return electrode, such that grasping the microcurrent TMJ treatment device makes an electrical coupling between a user's hand and the return electrode;

holding the microcurrent TMJ treatment device with a treatment electrode of the microcurrent TMJ treatment device in contact with a first skin surface location, the first skin surface location of the user corresponding to a predetermined location for affecting TMJ symptoms; and maintaining contact between the treatment electrode and the first skin surface location while the treatment electrode and return electrode of the microcurrent TMJ treatment device pass a biphasic waveform through a portion of the user's body including tissues subjacent the treatment electrode, and through the should, arm and hand, while the microcurrent TMJ treatment device maintains the biphasic waveform at a constant peak current level of 15 milliamps or less, wherein the biphasic waveform applies a peak microcurrent density of less than 250 milliamps per square centimeter at the first skin surface location to create a current path along a subjacent nerve, through the user's arm, and through the user's hand to the return electrode.

16. The treatment method of claim 15, wherein the biphasic waveform applies a peak current density greater than 50 milliamps per square centimeter at the first skin surface location.

17. The treatment method of claim 15, wherein the biphasic waveform applies a peak current density of about 100 milliamps per square centimeter at the first skin surface location.

18. The treatment method of claim 15, wherein the biphasic waveform has a peak current of less than 15 milliamps.

19. The treatment method of claim 15, wherein the biphasic waveform has a peak current of greater than 3 milliamps.

20. The treatment method of claim 15, wherein the biphasic waveform has a peak current of about 6 milliamps.

* * * * *